United States Patent [19]

Ginsburg

[11] Patent Number: 4,873,978
[45] Date of Patent: Oct. 17, 1989

[54] DEVICE AND METHOD FOR EMBOLI RETRIEVAL

[76] Inventor: Robert Ginsburg, 2489 Alpine Rd., Menlo Park, Calif. 94025

[21] Appl. No.: 128,770

[22] Filed: Dec. 4, 1987

[51] Int. Cl.⁴ .......................................... A61M 29/00
[52] U.S. Cl. ..................................... 128/345; 128/325
[58] Field of Search ................. 128/303 R, 325, 345, 128/749–759

[56] References Cited

U.S. PATENT DOCUMENTS

| | | | |
|---|---|---|---|
| 2,767,703 | 10/1956 | Nieburgs | 128/749 |
| 3,800,781 | 4/1974 | Zalucki | 128/749 |
| 3,952,747 | 4/1976 | Kimmell, Jr. | 128/303 |
| 4,403,612 | 9/1983 | Fogarty | 128/325 |
| 4,425,908 | 1/1984 | Simon | 128/325 |
| 4,619,246 | 10/1986 | Molgaard-Nielsen et al. | 128/345 |
| 4,643,184 | 2/1987 | Mobin-Uddin | 128/303 R |
| 4,685,458 | 8/1987 | Leckrone | 128/303.1 |
| 4,688,553 | 8/1987 | Metals | 128/325 |

FOREIGN PATENT DOCUMENTS

| | | | |
|---|---|---|---|
| 2580504 | 10/1986 | France | 128/303 R |
| 764684 | 9/1980 | U.S.S.R. | 128/325 |

OTHER PUBLICATIONS

Medi-Tech, Inc., Watertown, Mass., Bulletin VCF-1, May 1985.
English Translation of French Pat. No. 2,580,504 to Pieronne, Oct. 1986.

Primary Examiner—Max Hindenburg
Attorney, Agent, or Firm—Townsend and Townsend

[57] ABSTRACT

A vascular catheter includes a strainer device at its distal end. The strainer device is collapsible, capable of assuming both an open configuration where it is able to capture emboli when emplaced in a blood vessel, and a closed configuration where it is able to retain any captured emboli within its confines. The catheter of the present invention is normally utilized in conjunction with conventional angioplastic treatment techniques. By locating the strainer device downstream from the site of the angioplastic treatment, any emboli which are released during such treatment may be captured and removed from circulation.

13 Claims, 2 Drawing Sheets

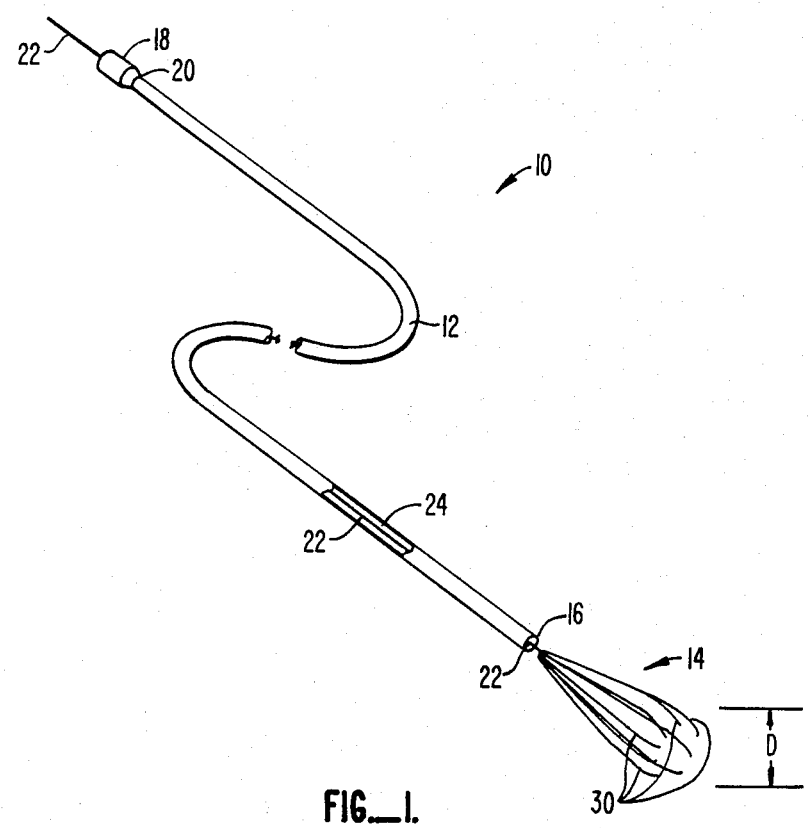
FIG._1.
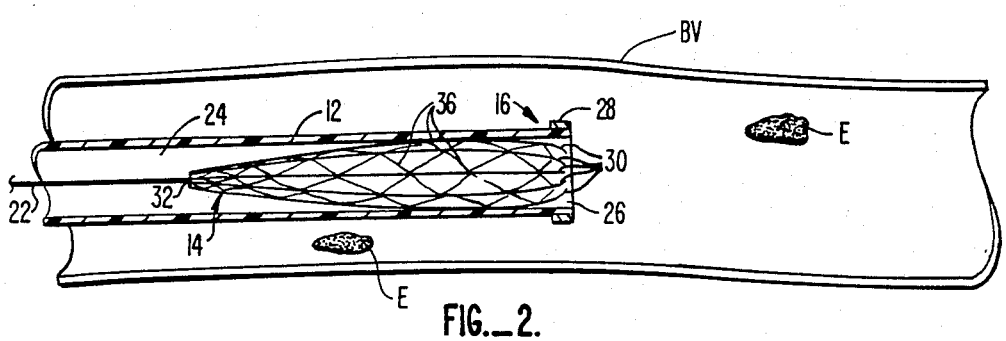
FIG._2.
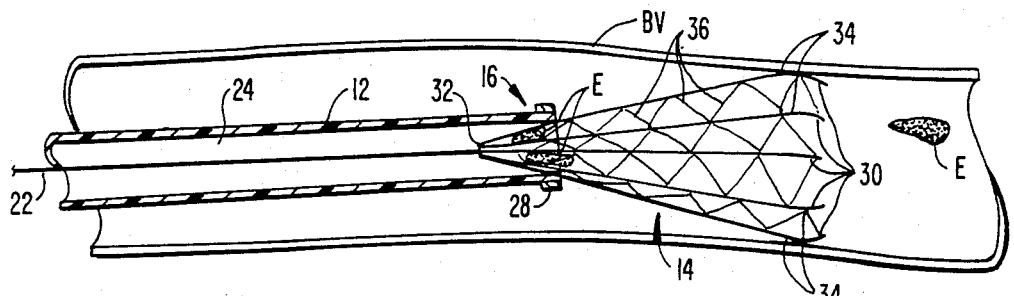
FIG._3.

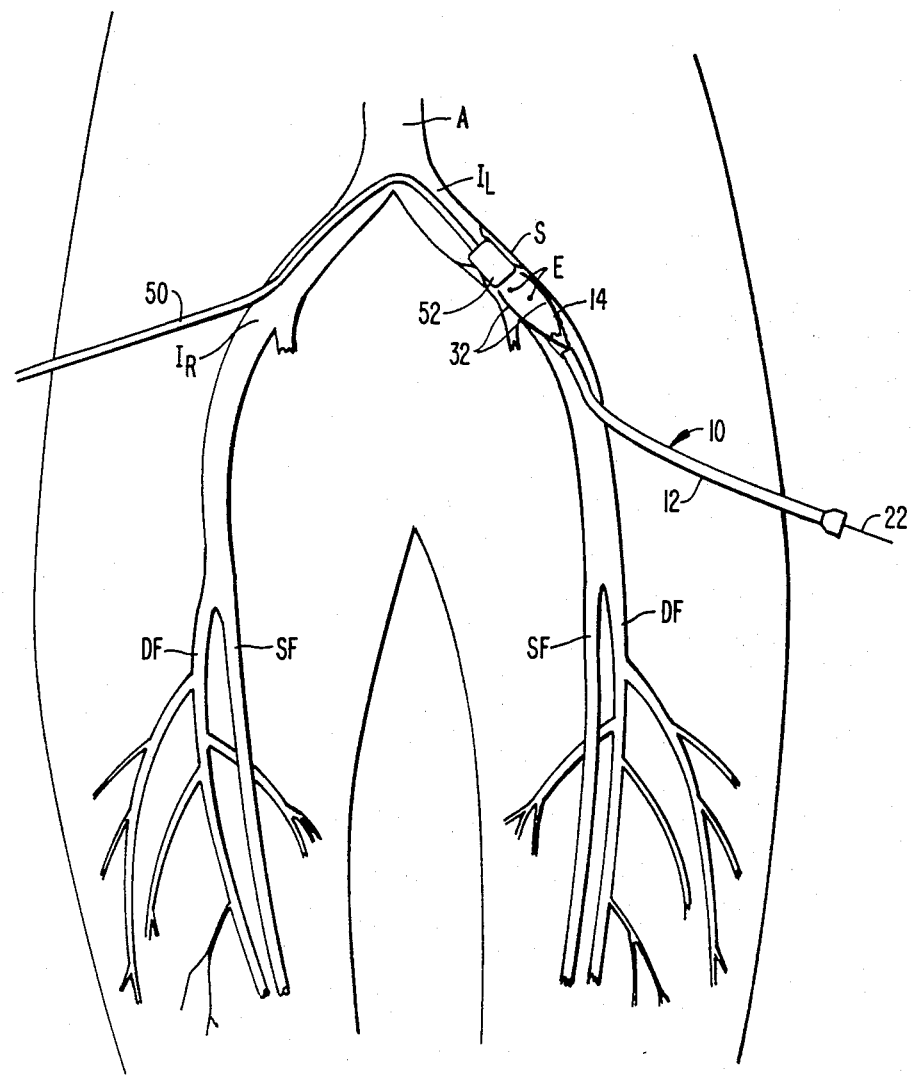
FIG._4.

DEVICE AND METHOD FOR EMBOLI RETRIEVAL

BACKGROUND OF THE INVENTION

1. Field of the Invention

The present invention relates generally to the construction and use of vascular catheters. More particularly, the invention is a catheter including a strainer device which is used for the intraarterial retrieval of emboli, normally while performing angioplastic procedures.

A variety of non-surgical angioplastic procedures have been developed for removing obstructions from blood vessels. Balloon angioplasty utilizes a balloon-tipped catheter which may be inserted within a stenosed region of the blood vessel. By inflating the balloon, the stenosed region is dilated. Laser angioplasty utilizes laser radiation for ablating a stenosed region. In theory, the plaque or thrombus is vaporized and dissolved in the bloodstream where it is eliminated by normal bodily functions. Other techniques, such as atherectomy and suction angioplasty have also been proposed. In atherectomy, a turning blade is used to shave plaque from an arterial wall while in suction angioplasty a vacuum is used to draw plaque or thrombus out of the blood vessel through a suitable catheter.

One problem common with all of these techniques is the accidental release of portions of the plaque or thrombus, resulting in emboli which can lodge elsewhere in the vascular system. Such emboli are, of course, extremely dangerous to the patient, frequently causing severe impairment of the circulatory system. Indeed, in the worst cases, multiple emboli are released which can so severely reduce peripheral blood circulation that amputation becomes necessary.

For these reasons, it would be highly desirable to provide an apparatus and method for preventing embolisms associated with conventional angioplastic procedures. In particular, it would be desirable to provide a device which could be located within the vascular system to collect and retrieve portions of clot and thrombus which are dislodged during the angioplastic procedure.

2. Description of the Background Art

U.S. Pat. No. 3,952,747 describes a stainless steel filtering device which is permanently implanted transvenously within the inferior vena cava. The filtering device is intended to treat recurrent pulmonary embolism. A device constructed pursuant to the teachings of the patent is sold by Medi-tech, Inc., Watertown, Massachusetts, as described in their Bulletin VCF-1.

SUMMARY OF THE INVENTION

According to the present invention, embolisms resulting from angioplastic treatment are avoided by the intraarterial capture and retrieval of emboli dislodged from the treatment site. More specifically, a strainer device is positioned within the patient's vascular system downstream from the treatment site, preferably prior to any bifurcation of the blood vessel being treated. During treatment, the strainer will entrap particles of clot and loose plaque which may be dislodged by the angioplastic treatment, preventing them from lodging in areas of more restricted flow within the vascular system. After the angioplastic treatment is completed, the strainer is closed or collapsed around the captured emboli, and the strainer and emboli are removed from the vascular system.

The catheter device of the present invention comprises a catheter body having a strainer mounted at its distal end. The strainer is shiftable between an opened configuration where it extends substantially across the blood vessel to entrap passing emboli, and a closed configuration where it retains the captured emboli during removal of the catheter. A mechanism actuable at the proximate end of the catheter body allows selective opening and closing of the strainer. Typically, the strainer will comprise a collapsible cone having an apex attached to a wire running from the distal end to the proximate end of the catheter body. The conical strainer is spring biased so that it assumes the open configuration when it is not otherwise constrained. In this way, the strainer may be closed by pulling on the wire and retracting the strainer within the opened distal end of the catheter body. Conversely, the strainer may be opened by pushing on the wire and extending the strainer from the distal end of the catheter body so that the strainer assumes its opened configuration.

BRIEF DESCRIPTION OF THE DRAWINGS

FIG. 1 illustrates a vascular catheter having a strainer device at its distal end, constructed in accordance with the principles of the present invention.

FIG. 2 is a detailed view of the distal end of the catheter of FIG. 1 located within a blood vessel, with the spring device being retracted in its closed configuration.

FIG. 3 is a view similar to FIG. 2, except that the strainer device has been extended forward of the catheter to assume its opened configuration.

FIG. 4 is a schematic view illustrating the use of the catheter of the present invention during balloon angioplasty of the iliac artery.

DESCRIPTION OF THE SPECIFIC EMBODIMENTS

Referring now to FIG. 1, a vascular catheter 10 constructed in accordance with the principles of the present invention includes an elongate catheter body 12 having a strainer device 14 mounted at its distal end 16. A sealable fitting 18 is mounted at the proximate end 20 of the catheter body 12, allowing the catheter body to be inserted into a desired position within a patient's vascular system over a guidewire (not illustrated). The fitting 18 also allows insertion and removal of the strainer 14 which is attached to control wire 22. As will be described in more detail hereinbelow, the strainer device 14 is capable of assuming an opened configuration (FIG. 3) where it extends substantially across the interior lumen of a blood vessel BV so that it is able to capture emboli E flowing through the vessel. Alternatively, the strainer device 14 is capable of assuming a closed configuration (FIG. 2) where it is withdrawn from the interior wall of the blood vessel and enclosed about any emboli E which had been entrapped while it was in its opened configuration. The strainer device 14 will be in the closed configuration of FIG. 2 whenever it is to be simultaneously inserted or withdrawn together with the catheter body 12.

The catheter body 12 includes an interior lumen 24 which receives the control wire 24. The distal end of the catheter body 12 defines an open port 26 and may include reinforcement, such as a metallic or rigid plastic reinforcement ring 28 (FIGS. 2 and 3). Additionally, the distal end 16 of the catheter body 12 may be somewhat enlarged (not illustrated) or may be formed as a separate piece (not illustrated) in order to receive the strainer device 14 in its closed configuration (FIG. 2).

The materials of construction for the catheter body 12 are not critical and will normally be those employed in constructing vascular catheters for other purposes. The catheter body 12 will typically be constructed of a physiologically-acceptable polymer, such as silicone rubber, natural rubber, polyvinylchloride, polyurethane, polyester, and the like. Conveniently, the polymer may include substances which render the catheter radiopaque so that it may be located by conventional radiological imaging techniques.

The length of the catheter body 12 is not critical and will depend on the desired location within the vascular system where the strainer 14 is to be emplaced. Typically, the length will be in the range from about 8 cm to 30 cm, usually being in the range from about 10 cm to 15 cm. The internal diameter of the catheter body is also not critical, although it should be sufficiently large to allow unrestricted passage of the control wire 22. The diameter may also vary over the length of the catheter body 12, with a greater diameter at the distal end 16 being provided to allow for retraction of the strainer 14, as discussed above. In cases where the strainer 14 is not to be passed through the catheter body 12, the diameter of the remaining length of the catheter body 12 may be substantially reduced since it only need accommodate the control wire 24. Conversely, in cases where the strainer 14 is to be inserted and withdrawn through the catheter body 12, the internal lumen 24 diameter will have to be sufficiently great along its entire length in order to accommodate the collapsed strainer 14. Typically, the internal lumen of the catheter 12 may vary in the range from about 2 to 10 French (1 Fr equals 0.013 inches), usually being between 4 and 8 Fr.

In the exemplary embodiment, the strainer device 14 includes a plurality of tines 30 attached to the distal end 32 of wire 22. Attachment may be accomplished by conventional techniques, such as a suitable eutectic braze. The tines are spring biased so that they assume an opened conical configuration (as illustrated in FIG. 1) when unconstrained. Typically, the spring biasing will derive from the inherent spring characteristic of the tine material itself That is, the tines will be attached to the distal end 32 in an outwardly diverging manner to form a generally conical shape having a desired diameter at the base of the cone. The tines, however, may be collapsed by applying an inward, diverging pressure along their length to assume the configuration of Fi. 2. Alternatively, a separate spring biasing device (not illustrated) may be provided to urge the tines to open when unconstrained. As a second alternative, the tines could be connected to the distal end 32 of wire 22 by articulated joints so that they are unbiased. In the latter case, it would be necessary to provide a separate means (not illustrated) for opening the tines outward when the strainer device 14 is at the desired location within the blood vessel BV.

The base of the cone defined by tines 30 will have a diameter D (FIG. 1) sufficiently large so that the tines will extend across the interior lumen of the blood vessel where the strainer 14 is to be emplaced. Typically, the diameter D will be in the range from about 4 to 12 Fr, more usually in the range from about 6 to 10 Fr. Of course, strainer devices 14 having a range of different sizes may be fabricated for use in different blood vessels BV.

The tines 32 will usually be constructed of a spring metal, more usually being stainless steel, although various rigid plastics and other biocompatible materials might also find use. In their unbiased state, the tines 32 will generally be straight but terminate at their distal end in a curved tip 34. The curve tip 34 facilitates extension of the strainer 14 into the blood vessel BV and retraction of the strainer from the blood vessel. Although the exemplary embodiment illustrates straight tines 32, there is no reason why other configurations and geometries, such as serpentine, twisted, irregular, flattened, and the like, might not also find use. The strainer 14 might also include lateral members 36 extending between adjacent tines 32, as illustrated in FIGS. 2 and 3. The lateral members 36 may be rigid, typically formed from rigid metal or plastic elements, or may be resilient, typically formed from elastomeric polymers. The lateral members 36 enhance the ability of the strainer device 14 to capture and entrap emboli E.

The length of the tines 32 may vary substantially, but will typically be within the range from about 2 to 10 cm, more typically being in the range from about 3 to 8 cm. By utilizing such relatively-long tines, the conical strainer 1 is greatly elongated, increasing its internal volume. Such increased internal volume allows the retention of a relatively great amount of emboli material to be retained within the strainer device 14 without blockage of the arterial flow.

Referring now to FIG. 4, use of the vascular catheter 10 of the present invention for capturing emboli dislodged during balloon angioplasty of a stenosed region S in the iliac artery I will be described. A balloon catheter 50 is inserted into the patient's left iliac artery $I_L$ by access through the right iliac artery $I_R$. Catheter 50 is inserted and passed around the bifurcation of the abdominal artery A, as illustrated, so that balloon tip 52 lies within the region of stenosis S 50.

Prior to dilation of the balloon 52, catheter 10 of the present invention is inserted into the left iliac artery $I_L$ in a retrograde orientation. The strainer device 14 is located immediately downstream from the stenosed region S, and the strainer extended so that tines 32 assume their opened configuration. Preferably, the strainer 14 will be immediately downstream from the stenosed region, prior to any bifurcation of the artery.

Once the strainer device 14 is positioned and opened (as illustrated in FIG. 3), the balloon 52 may be inflated to dilate the stenosed region S. Any emboli released from the stenosed region S will then be captured by the strainer device, rather than passing down the iliac into the deep femoral artery DF or the superficial femoral artery SF. It will be appreciated that these arteries undergo substantial branching so that emboli passing downward will likely become lodged in the branches and capillaries, causing widespread embolisms.

Although illustrated in connection with balloon angioplasty, it will be appreciated that the catheter device 10 of the present invention may be utilized in connection with virtually any other type of angioplastic treatment, such as laser angioplasty, suction angioplasty, atherectomy, and the like, which might result in the release of emboli from a region of stenosis.

Additionally, it will be appreciated that the catheter 10 may be emplaced within the iliac artery $I_L$ by conventional techniques. Conveniently, the catheter body 12 may first be inserted over a guidewire. Thereafter, the catheter device 14 on wire 22 may be inserted through the catheter body 12 and eventually extended from the distal end of the catheter body to assume its open configuration. Alternatively, the catheter device 10 may be inserted with the strainer device 14 in place within the catheter body 12. Once the catheter body 12 is in position, the catheter device 14 will be extended as described previously.

Once the angioplastic treatment is concluded, the balloon 52 will be deflated, and the vascular catheter 50 removed. After the vascular catheter 50 has been removed, the strainer device 14 may be collapsed about any entrapped emboli E by retracting said strainer into the open port 26 of the catheter device 10. The strainer 14 may then either be withdrawn completely from the catheter body 12, or may be withdrawn together with the catheter body 12 as the catheter device 10 is removed, in a conventional manner.

Although the foregoing invention has been described in some detail by way of illustration and example for purposes of clarity of understanding, it will be obvious that certain changes and modifications may be practiced within the scope of the appended claims.

What is claimed is:

1. A catheter device for capturing and retrieving emboli from a blood vessel, said catheter device comprising:
   an elongate catheter body having a proximate end and a distal end;
   a strainer mounted at the distal end of the catheter body, said strainer comprising a plurality of tines which are shiftable between an opened configuration where they are capable of capturing emboli and a closed configuration where they are capable of retaining captured emboli, said tines having inwardly curved tips; and
   means actuable from the proximate end for selectively shifting the tines of the strainer between the opened configuration and the closed configuration.

2. A catheter device as in claim 1, wherein the catheter body includes a receptacle at its distal end and wherein the strainer is oriented in the opened configuration while outside of the receptacle and the closed configuration while inside the receptacle.

3. A catheter device as in claim 2, wherein the receptacle is defined by the distal end of an axial lumen extending between the proximate and distal ends of the catheter body.

4. A catheter device as in claim 3, wherein the means for selectively shifting the strainer is a wire fixedly attached at one end to the strainer and extending ending through the axial lumen to the proximate end of the catheter body.

5. A method for percutaneous transluminal angioplasty, said method comprising:
   introducing a first vascular catheter to a stenosed region within a vascular system;
   introducing a second vascular catheter to a location in the vascular system downstream from the stenosed region;
   treating the stenosed region with the first vascular catheter, whereby emboli may be shed into circulation within the vascular system;
   capturing the emboli with the second vascular catheter; and
   withdrawing the second vascular catheter with the captured emboli.

6. A method as in claim 5, wherein the first vascular catheter is a balloon-tipped catheter and the stenosed region is treated by dilation.

7. A method as in claim 5, wherein the first vascular catheter is a laser catheter and the stenosed region is treated by ablation.

8. A method as in claim 5, wherein the first vascular catheter is a blade-tipped catheter and the stenosed region is treated by atherectomy.

9. A method as in claim 5, wherein the second vascular catheter includes a strainer mounted at its distal end for capturing the emboli.

10. A method as in claim 9, wherein the emboli are captured while the strainer is in an open configuration and the second vascular catheter is withdrawn while the strainer is in a closed configuration.

11. A catheter device for capturing and retrieving emboli from a blood vessel, said catheter device comprising:
    an elongate catheter body having a proximate end, a distal end, and an axial lumen extending between said proximate and distal ends;
    a wire extending through the lumen and having proximate and distal ends; and
    a conical strainer having an apex secured to the distal end of the wire, said strainer being collapsible so that it assumes an opened configuration when extended out from the distal end of the catheter body and a closed configuration when retracted into the distal end of the catheter body, wherein the conical strainer comprises a plurality of generally axial members having inwardly curved tips at their distal ends and are secured together at the apex.

12. A catheter device as in claim 11, wherein the axial members are spring biased to spread apart when the conical strainer is extended out from the catheter and to collapse when the conical strainer is retracted into the catheter.

13. A catheter device as in claim 11, wherein the conical strainer includes transverse elements extending between the axial members.

* * * * *